(12) United States Patent
Pandev et al.

(10) Patent No.: US 10,345,095 B1
(45) Date of Patent: Jul. 9, 2019

(54) MODEL BASED MEASUREMENT SYSTEMS WITH IMPROVED ELECTROMAGNETIC SOLVER PERFORMANCE

(71) Applicant: KLA-Tencor Corporation, Milpitas, CA (US)

(72) Inventors: Stilian Ivanov Pandev, Santa Clara, CA (US); Leonid Poslavsky, Belmont, CA (US); Dzmitry Sanko, Vallejo, CA (US); Andrei V. Shchegrov, Campbell, CA (US)

(73) Assignee: KLA- Tencor Corporation, Milpitas, CA (US)

( * ) Notice: Subject to any disclaimer, the term of this patent is extended or adjusted under 35 U.S.C. 154(b) by 612 days.

(21) Appl. No.: 14/947,510

(22) Filed: Nov. 20, 2015

Related U.S. Application Data

(60) Provisional application No. 62/082,140, filed on Nov. 20, 2014.

(51) Int. Cl.
*G01B 11/06* (2006.01)
*G01B 11/02* (2006.01)
(Continued)

(52) U.S. Cl.
CPC .............. *G01B 11/06* (2013.01); *G01B 11/02* (2013.01); *G01B 21/08* (2013.01); *H01L 22/12* (2013.01);
(Continued)

(58) Field of Classification Search
CPC . G01B 11/06; G01B 5/06; G01B 9/04; G01B 2210/44; G01B 11/02; G01B 21/08;
(Continued)

(56) References Cited

U.S. PATENT DOCUMENTS

| 5,608,526 A | 3/1997 | Piwonka-Corle et al. |
| 5,859,424 A | 1/1999 | Norton et al. |

(Continued)

*Primary Examiner* — Sujoy K Kundu
*Assistant Examiner* — Lynda Dinh
(74) *Attorney, Agent, or Firm* — Spano Law Group; Joseph S. Spano

(57) ABSTRACT

Methods and systems for solving measurement models of complex device structures with reduced computational effort are presented. In some embodiments, a measurement signal transformation model is employed to compute transformed measurement signals from coarse measurement signals. The transformed measurement signals more closely approximate a set of measured signals than the coarse measurement signals. However, the coarse set of measured signals are computed with less computational effort than would be required to directly compute measurement signals that closely approximate the set of measured signals. In other embodiments, a measurement signal transformation model is employed to compute transformed measurement signals from actual measured signals. The transformed measurement signals more closely approximate the coarse measurement signals than the actual measured signals. Transformed measurement signals are subsequently used for regression, library generation, or other analyses typically employed as part of an effort to characterize structural, material, and process parameters in semiconductor manufacturing.

20 Claims, 11 Drawing Sheets

(51) Int. Cl.
  G01B 21/08 (2006.01)
  H01L 21/66 (2006.01)
  *G01N 21/95* (2006.01)
  *G01N 21/88* (2006.01)
  *G01N 21/64* (2006.01)

(52) U.S. Cl.
  CPC ...... *G01B 2210/44* (2013.01); *G01B 2290/45* (2013.01); *G01N 21/8806* (2013.01); *G01N 21/9501* (2013.01); *G01N 2021/6421* (2013.01)

(58) Field of Classification Search
  CPC ............... G01B 2290/45; H01L 22/12; G01N 21/9501; G01N 21/8806; G01N 2021/6421
  USPC ......................................................... 702/155
  See application file for complete search history.

(56) References Cited

U.S. PATENT DOCUMENTS

| | | | |
|---|---|---|---|
| 6,429,943 B1 | 8/2002 | Opsal et al. | |
| 6,633,831 B2 | 10/2003 | Nikoonahad et al. | |
| 6,734,967 B1 | 5/2004 | Piwonka-Corle et al. | |
| 6,816,570 B2 | 10/2004 | Janik et al. | |
| 6,895,075 B2 | 5/2005 | Yokhin et al. | |
| 6,972,852 B2 | 12/2005 | Opsal et al. | |
| 7,478,019 B2 | 1/2009 | Zangooie et al. | |
| 7,826,071 B2 | 11/2010 | Shchegrov et al. | |
| 7,929,667 B1 | 4/2011 | Zhuang et al. | |
| 7,933,026 B2 | 4/2011 | Opsal et al. | |
| 2009/0063075 A1* | 3/2009 | Liu | G01B 11/24 702/82 |
| 2011/0288822 A1* | 11/2011 | Veldman | G02B 5/1847 702/189 |
| 2013/0006539 A1* | 1/2013 | Di | G01N 21/211 702/28 |
| 2013/0114085 A1 | 5/2013 | Wang et al. | |
| 2014/0111791 A1 | 4/2014 | Manassen et al. | |
| 2014/0172394 A1 | 6/2014 | Kuznetsov et al. | |
| 2014/0222380 A1 | 8/2014 | Kuznetsov et al. | |
| 2014/0297211 A1 | 10/2014 | Pandev et al. | |
| 2014/0316730 A1 | 10/2014 | Shchegrov et al. | |
| 2015/0042984 A1 | 2/2015 | Pandev et al. | |
| 2015/0046118 A1 | 2/2015 | Pandev et al. | |

* cited by examiner

MODEL BASED MEASUREMENT SYSTEMS WITH IMPROVED ELECTROMAGNETIC SOLVER PERFORMANCE

CROSS REFERENCE TO RELATED APPLICATION

The present application for patent claims priority under 35 U.S.C. § 119 from U.S. provisional patent application Ser. No. 62/082,140, entitled "Process Window Based EM Engine Performance Optimization," filed Nov. 20, 2014, the subject matter of which is incorporated herein by reference in its entirety.

TECHNICAL FIELD

The described embodiments relate to metrology systems and methods, and more particularly to methods and systems for model based measurement with reduced computational effort.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Optical metrology processes are used at various steps during a semiconductor manufacturing process to detect defects on wafers to promote higher yield. Optical metrology techniques offer the potential for high throughput without the risk of sample destruction. A number of optical metrology based techniques including scatterometry and reflectometry implementations and associated analysis algorithms are commonly used to characterize critical dimensions, film thicknesses, process parameters, composition and other parameters of nanoscale structures.

As devices (e.g., logic and memory devices) move toward smaller nanometer-scale dimensions, characterization becomes more difficult. Devices incorporating complex three-dimensional geometry and materials with diverse physical properties contribute to characterization difficulty.

In response to these challenges, more complex optical tools have been developed. Measurements are performed over a large ranges of several machine parameters (e.g., wavelength, azimuth and angle of incidence, etc.), and often simultaneously. As a result, the measurement time, computation time, and the overall time to generate reliable results, including measurement recipes, increases significantly.

Existing model based metrology methods typically include a series of steps to model and then measure structure parameters. Typically, measurement data (e.g., DOE spectra) is collected from a particular metrology target. An accurate measurement model of the optical system, dispersion parameters, and geometric features is formulated. An electromagnetic (EM) solver is employed to solve the measurement model and predict measurement results. A series of simulations, analysis, and regressions are performed to refine the geometric model and determine which model parameters to float. In some examples, a library of synthetic spectra is generated. Finally, measurements are performed using the library or regression in real time with the geometric model. The EM simulation process is controlled by a number of parameters (e.g., slabbing parameters, Rigorous Coupled Wave Analysis (RCWA) parameters, discretization parameters, etc.). Simulation parameters are selected to avoid introducing excessively large errors. However, in general, there is a trade-off between computational effort and solution accuracy. In other words, an accurate solution requires much more computational effort than a less accurate solution. Currently, the computational effort required to arrive at sufficiently accurate measurement results for complex semiconductor structures is large and growing larger.

Many current systems employ a RCWA algorithm to solve the measurement model. Simulated measurement signals are computed by the RCWA engine. Measured signals are compared to the computed signals as part of a regression analysis to estimate measurement parameter values. When current systems are employed to measure complex geometric structures, three dimensional structures, and large pitch structures, a high truncation order is necessary to accurately represent the corresponding physical measurement signals. This significantly increases the required computational effort. In a further example, simulated measurement signals are integrated for multiple angles of incidence present in the optical path of the measurement system. This is commonly referred to as "NA integration." Computational effort increases proportionally with the number of angles.

To meet the increasing computational burden, large computing clusters are required, and in some cases it is impractical to perform the necessary computations for some models. Although a lower truncation order or reduced NA integration may be employed to reduce the required computational effort, this often results in unacceptably large measurement errors.

Increasingly complicated measurement models are causing corresponding increases in computational effort. Improved model solution methods and tools are desired to arrive at sufficiently accurate measurement results with reduced computational effort.

SUMMARY

Methods and systems for solving measurement models of complex device structures with reduced computational effort are presented. Metrology systems employing these techniques are configured to measure process parameters and structural and material characteristics (e.g., material composition, dimensional characteristics of structures and films, etc.) associated with different semiconductor fabrication processes.

In one aspect, a measurement signal transformation model is employed to compute transformed measurement signals from coarse measurement signals. The coarse measurement signals are computed by a measurement model simulator. The transformed measurement signals more closely approximate a set of measured signals than the coarse measurement signals. However, the coarse set of measured signals are computed with less computational effort than would be required to directly compute measurement signals that closely approximate the set of measured signals. The transformed measurement signals are subsequently used for regression, library generation, or other analyses where simulated model based measurement signals are typically employed as part of an effort to characterize structural, material, and process parameters in semiconductor manufacturing.

In some examples, coarse measurement signals are simulated by a Rigorous Coupled Wave Analysis (RCWA) engine with a low truncation order (TO) approximation. In some other examples, coarse measurement signals are generated by an RCWA engine with a small number of slabs or coarsely approximated geometry. In some other examples, coarse measurement signals are generated with sparse Numerical Aperture (NA) sampling. In some other examples, coarse measurement signals are generated using different truncation order numbers and truncation order sampling patterns. A measurement signal transformation model is used to reconstruct physically meaningful signals from these coarse measurement signals.

In a further aspect, a measurement signal transformation model transforms coarse measurement signals of one signal type to physically meaningful signals of another signal type required for successful measurement.

In yet another further aspect, a measurement signal transformation model transforms multiple coarse measurement signals of one or more different types to physically meaningful signals of another different type required for successful measurement.

In yet another further aspect, a measurement signal transformation model is trained to compute transformed measurement signals from coarse measurement signals. Machine learning is used to determine the relationship between coarse measurement signals and corresponding physical signals, and train the measurement signal transformation model based on a DOE training set of data. In this manner, a mathematical function relating coarse measurement signals to transformed signals that accurately reconstruct corresponding physical measurement signals is obtained.

In yet another further aspect, a combination of different simulators may be employed to compute measurement signals as described herein. In some examples, the type of simulator employed to generate coarse measurement signals is different from the type of simulator employed to generate measured signals that accurately reconstruct physical measurement signals.

In yet another further aspect, the measurement signals described may include derivatives of measurement signals with respect to parameters of interest or system parameters. These derivatives may be used for regression or other fitting algorithms.

In another aspect, a measurement signal transformation model is employed to compute transformed measurement signals from actual measured signals. In addition, coarse measurement signals are computed by a measurement model simulator. The transformed measurement signals more closely approximate the coarse measurement signals than the actual measured signals. The transformed measurement signals are subsequently used for regression, library generation, or other analyses where simulated model based measurement signals are typically employed as part of an effort to characterize structural, material, and process parameters in semiconductor manufacturing.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Figure 1:
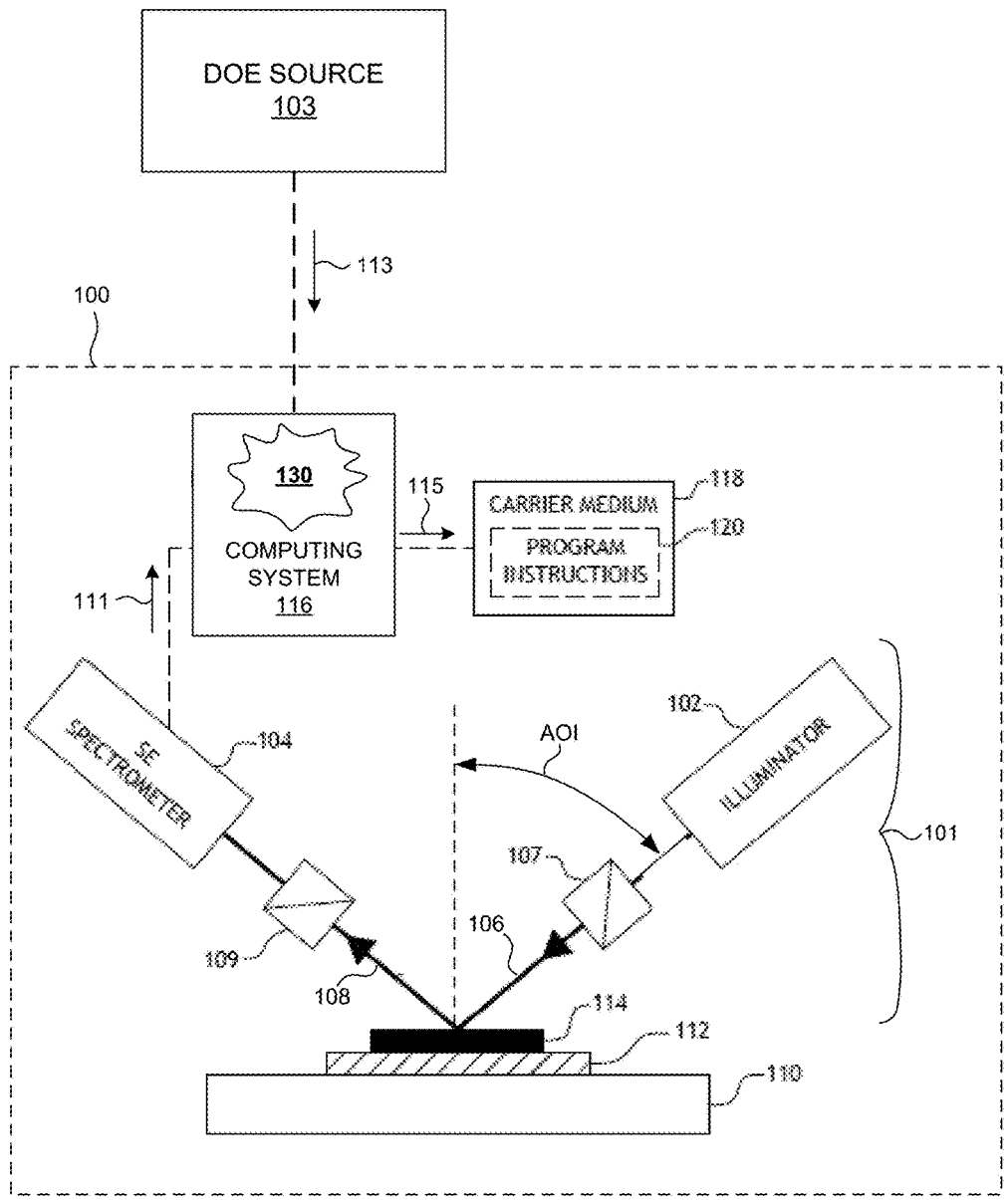
FIG. 1 illustrates a system 100 for measuring characteristics of a semiconductor wafer.

Reference will now be made in detail to background examples and some embodiments of the invention, examples of which are illustrated in the accompanying drawings.

Methods and systems for solving measurement models of complex device structures with reduced computational effort are presented. Metrology systems employing these techniques are configured to measure process parameters and structural and material characteristics (e.g., material composition, dimensional characteristics of structures and films, etc.) associated with different semiconductor fabrication processes.

In general, model based measurement signals simulated with smaller approximations more closely track physical signals than measurement signals simulated with larger approximations. Hence, intuitively, one would assume that measurement signals simulated with larger approximations would not be suitable for model based parameter estimation, while measurement signals computed with smaller approximations result in improved measurement accuracy. In fact, this has been the trend in the industry for many years. However, the inventors have unexpectedly discovered that for typical process windows, measurement signals simulated with larger approximations (e.g., low truncation order, sparse NA sampling, small number of slabs, etc.) contain nearly the same sensitivity to measurement parameters as measurement signals computed with smaller approximations (e.g., high truncation order, fine NA sampling, large number of slabs, etc.). The inventors have found that although, measurement signals simulated with larger approximation do not closely resemble corresponding physically measured signals, they contain the information needed to perform accurate model based measurements.

In one aspect, a measurement signal transformation model is employed to compute transformed measurement signals from coarse measurement signals. The coarse measurement signals are computed by a measurement model simulator. The transformed measurement signals more closely approximate a set of measured signals than the coarse measurement signals. However, the coarse set of measured signals are computed with less computational effort than would be required to directly compute measurement signals that closely approximate the set of measured signals. The transformed measurement signals are subsequently used for regression, library generation, or other analyses where simulated model based measurement signals are typically employed as part of an effort to characterize structural, material, and process parameters in semiconductor manufacturing.

Transforming coarse measurement signals with a measurement signal transformation model significantly reduces the computational effort associated with all RCWA computations, including regression, library generation, and other analyses. Furthermore, previously impractical measurement models of large pitch and complex three dimensional structures are solved with reasonable computational effort. In some measurement applications, real-time regression is enabled and measurement accuracy is improved.

FIG. 1 illustrates a system 100 for measuring characteristics of a semiconductor wafer. As shown in FIG. 1, the system 100 may be used to perform spectroscopic ellipsometry measurements of one or more structures 114 of a semiconductor wafer 112 disposed on a wafer positioning system 110. In this aspect, the system 100 may include a spectroscopic ellipsometer equipped with an illuminator 102 and a spectrometer 104. The illuminator 102 of the system 100 is configured to generate and direct illumination of a selected wavelength range (e.g., 150-1700 nm) to the structure 114 disposed on the surface of the semiconductor wafer 112. In turn, the spectrometer 104 is configured to receive light from the surface of the semiconductor wafer 112. It is further noted that the light emerging from the illuminator 102 is polarized using a polarization state generator 107 to produce a polarized illumination beam 106. The radiation reflected by the structure 114 disposed on the wafer 112 is passed through a polarization state analyzer 109 and to the spectrometer 104. The radiation received by the spectrometer 104 in the collection beam 108 is analyzed with regard to polarization state, allowing for spectral analysis of radiation passed by the analyzer. These spectra 111 are passed to the computing system 116 for analysis of the structure 114.

In a further embodiment, metrology system 100 includes one or more computing systems 116 configured to execute model based measurement tool 130 including measurement signal transformation functionality in accordance with the description provided herein. In the preferred embodiment, the model based measurement tool 130 is a set of program instructions 120 stored on a carrier medium 118. The program instructions 120 stored on the carrier medium 118 are read and executed by computing system 116 to realize model based measurement functionality as described herein. The one or more computing systems 116 may be communicatively coupled to the spectrometer 104. In one aspect, the one or more computing systems 116 are configured to receive measurement data 111 associated with a measurement (e.g., critical dimension, film thickness, composition, process, etc.) of the structure 114 of specimen 112. In one example, the measurement data 111 includes an indication of the measured spectral response of the specimen by measurement system 100 based on the one or more sampling processes from the spectrometer 104. In some embodiments, the one or more computing systems 116 are further configured to determine specimen parameter values of structure 114 from measurement data 111. In one example, the one or more computing systems 116 are configured to access model parameters in real-time, employing Real Time Critical Dimensioning (RTCD), or it may access libraries of precomputed models for determining a value of at least one specimen parameter value associated with the target structure 114.

In addition, in some embodiments, the one or more computing systems 116 are further configured to receive Design of Experiments (DOE) sample data 113 from a DOE source 103 such as an external computing system storing DOE sample data. The one or more computer systems are further configured to train measurement signal transformation models as described herein.

In some embodiments, measurement system 100 is further configured to store estimated parameter values 115 in a memory (e.g., carrier medium 118).

It should be recognized that the various steps described throughout the present disclosure may be carried out by a single computer system 116 or, alternatively, a multiple computer system 116. Moreover, different subsystems of the system 100, such as the spectroscopic ellipsometer 101, may include a computer system suitable for carrying out at least a portion of the steps described herein. Therefore, the aforementioned description should not be interpreted as a limitation on the present invention but merely an illustration. Further, the one or more computing systems 116 may be configured to perform any other step(s) of any of the method embodiments described herein.

The computing system 116 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium. In general, computing system 116 may be integrated with a measurement system such as measurement system 100, or alternatively, may be separate from any measurement system. In this sense, computing system 116 may be remotely located and receive measurement data and DOE sample data 113 from any measurement source and DOE source, respectively.

Program instructions 120 implementing methods such as those described herein may be transmitted over or stored on carrier medium 118. The carrier medium may be a transmission medium such as a wire, cable, or wireless transmission link. The carrier medium may also include a computer-readable medium such as a read-only memory, a random access memory, a magnetic or optical disk, or a magnetic tape.

In addition, the computer system 116 may be communicatively coupled to the spectrometer 104 or the illuminator subsystem 102 of the ellipsometer 101, or the user input source 103 in any manner known in the art.

The computing system 116 may be configured to receive and/or acquire data or information from the user input source 103 and subsystems of the system (e.g., spectrometer 104, illuminator 102, and the like) by a transmission medium that may include wireline and/or wireless portions. In this manner, the transmission medium may serve as a data link between the computer system 116, user input source 103, and other subsystems of the system 100. Further, the computing system 116 may be configured to receive measurement data via a storage medium (i.e., memory). For instance, the spectral results obtained using a spectrometer of ellipsometer 101 may be stored in a permanent or semi-permanent memory device (not shown). In this regard, the spectral results may be imported from an external system. Moreover, the computer system 116 may send data to external systems via a transmission medium.

The embodiments of the system 100 illustrated in FIG. 1 may be further configured as described herein. In addition, the system 100 may be configured to perform any other block(s) of any of the method embodiment(s) described herein.

Figure 2:
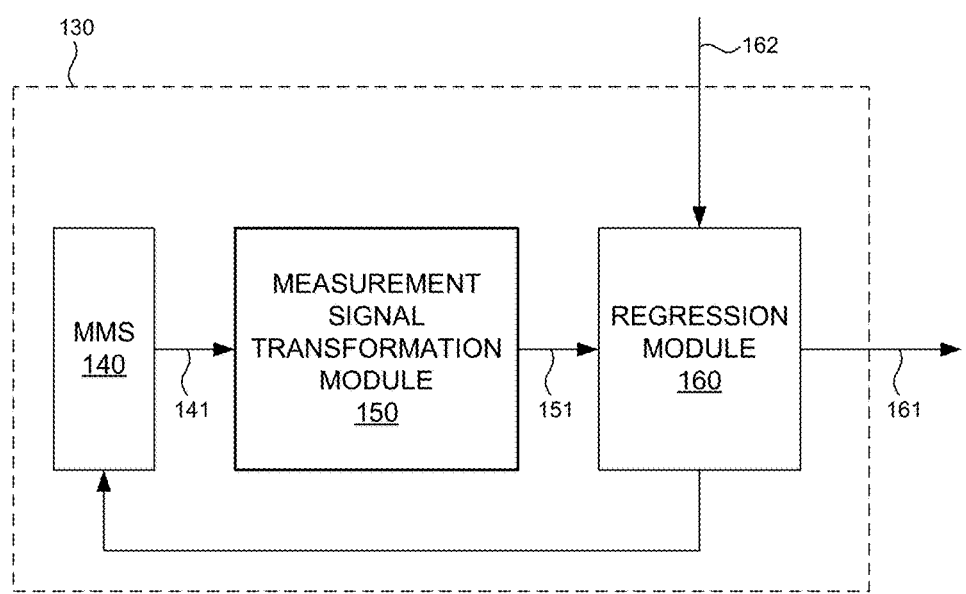
FIG. 2 depicts model based measurement tool 130 in one embodiment.

FIG. 2 depicts model based measurement tool 130 in one embodiment. As depicted in FIG. 2, model based measurement tool 130 includes a measurement model simulator (MMS) 140, measurement signal transformation module 150, and regression module 160. MMS 140 is a simulation engine configured to simulate a model of the entire measurement process. Typically, the measurement model includes geometric, material, and optical models of the measurement system and specimen under measurement. These models include physical dimensions, material properties, optical properties, and parameterization of the measurement system and the structure under measurement.

The simulation results provided by MMS 140 depend on the configuration of the measurement model itself (e.g., fixed model parameter values, floated model parameters, etc.) and various simulation parameters (e.g., number of slabs, truncation order, truncation pattern, etc.). The computational effort required to solve the measurement model depends greatly on the selected model and simulation parameters. As described hereinbefore, there is typically a trade-off between computational effort and accuracy of simulation results. Conventional measurement systems do not employ measurement signal transformation module 150. As such, model and simulation parameters must be selected such that MMS 140 is able to simulate measurement signals with sufficient accuracy to enable a stable convergence of estimated parameter values 161 by regression module 160. In some examples, this is only possible with an unacceptably large computational effort.

Figure 3:
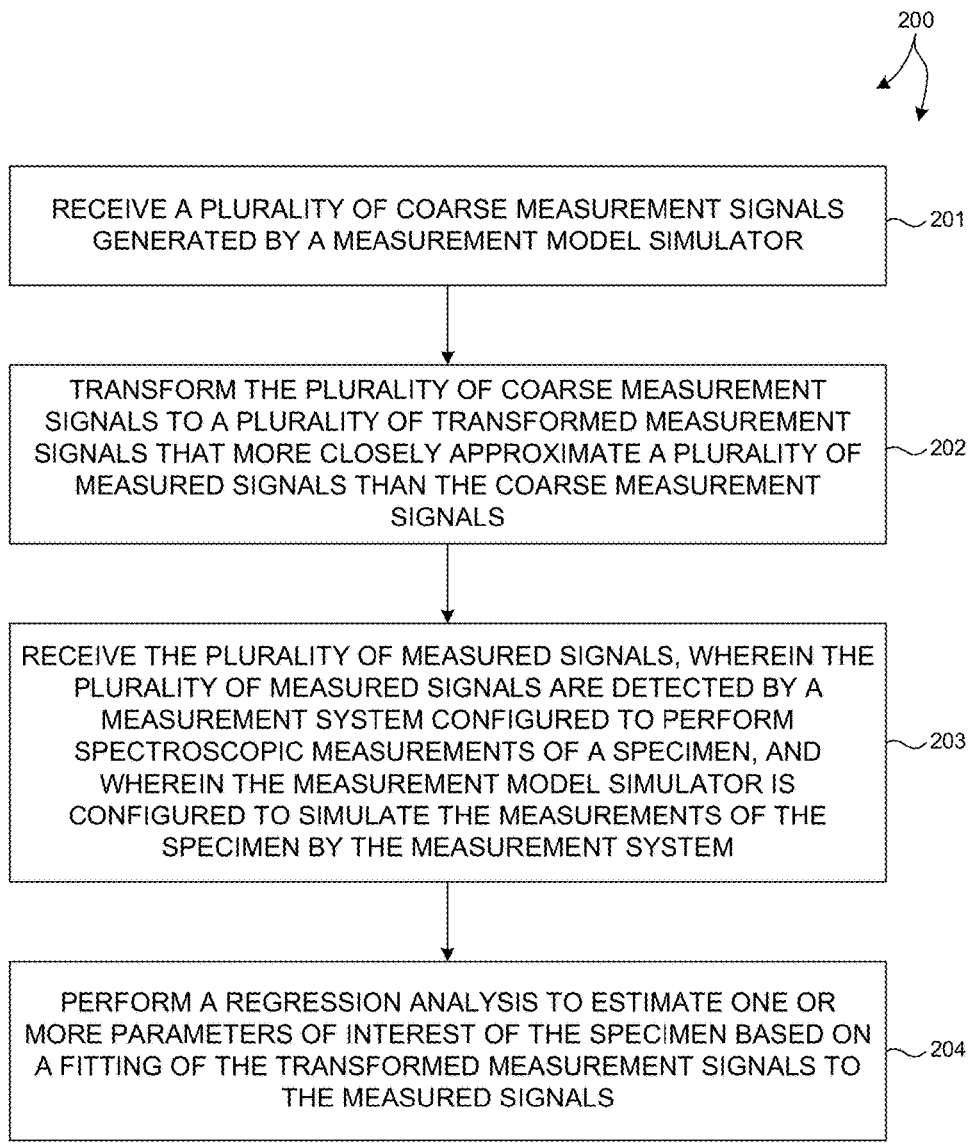
FIG. 3 illustrates a method 200 suitable for implementation by model based measurement tool 130 illustrated in FIG. 2 of the present invention.

FIG. 3 illustrates a method 200 suitable for implementation by model based measurement tool 130 illustrated in FIG. 2 of the present invention. In one aspect, it is recognized that data processing blocks of method 200 may be carried out via a pre-programmed algorithm executed by one or more processors of computing system 116, or any other general purpose computing system. It is recognized herein that the particular structural aspects of model based measurement tool 130 do not represent limitations and should be interpreted as illustrative only.

In block 201, measurement signal transformation module 150 receives a plurality of coarse measurement signals 141 generated by MMS 140. Measurement model and simulation parameters are selected such that MMS 140 generates coarse measurement signals 141 with less computational effort than would be required to generate high accuracy measurement signals suitable for stable convergence of estimated parameter values 161 by regression module 160. In these examples, the model and simulation parameter settings are suboptimal, yet this selection is made to reduce computational effort.

In block 202, measurement signal transformation module 150 transforms the plurality of coarse measurement signals 141 to a plurality of transformed measurement signals 151 that more closely approximate the plurality of measured signals 162 than the coarse measurement signals 141. Transformed measurement signals 151 are sufficiently accurate to ensure stable convergence of estimated parameter values 161 by regression module 160. In general, measured signals 162 may be actual measurement signals or synthetically generated measurements signals, or some combination.

In one example, MMS 140 is a Rigorous Coupled Wave Analysis (RCWA) engine simulated with a low truncation order (TO) approximation. The coarse measurement signals produced by the RCWA simulation do not resemble actual physical signals such as measured signals 162. However, the coarse measurement signals contain the information needed to successfully reconstruct a physically meaningful signal needed for successful measurement. The measurement transformation module 150 is used to reconstruct physically meaningful signals from the low truncation order signals.

In another example, measurement transformation module 150 transforms coarse measurement signals 141 generated by MMS 140 with a small number of slabs or coarsely approximated geometry to physically meaningful signals required for successful measurement.

In another example, measurement transformation module 150 transforms coarse measurement signals 141 generated by MMS 140 with sparse Numerical Aperture (NA) sampling to physically meaningful signals required for successful measurement. In these examples, a sparse selection of rays is simulated by MMS 140 to estimate measurement results for illumination over a broad NA.

In another example, each of the coarse measurement signals 141 are simulated using a different truncation order number and truncation order sampling pattern. In one example, critical parameters of a grating structure are more sensitive to illumination within the ultraviolet range of a spectroscopic ellipsometry (SE) system. In this example, a higher truncation order number and a denser truncation order pattern is set within this wavelength range. In addition, a lower truncation order number and a sparser truncation order sampling pattern is set outside this wavelength range.

Figure 5A:
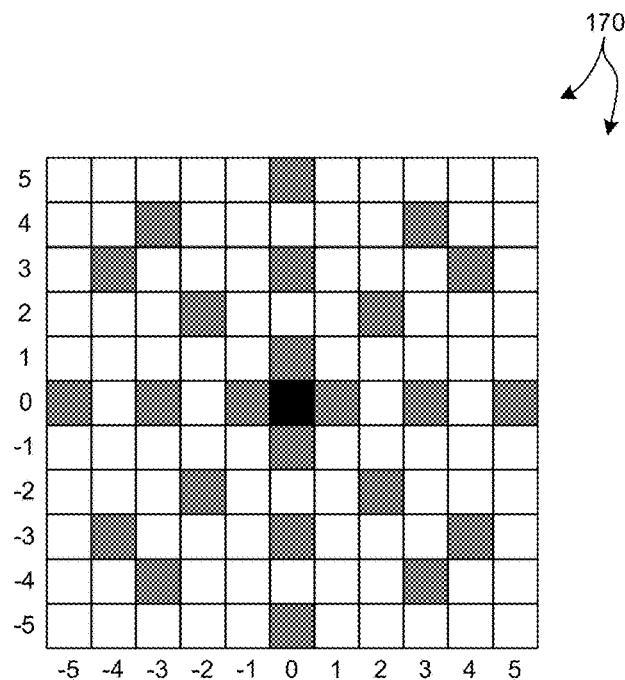
FIG. 5A depicts a relatively dense truncation order sampling pattern 170.
Figure 5B:
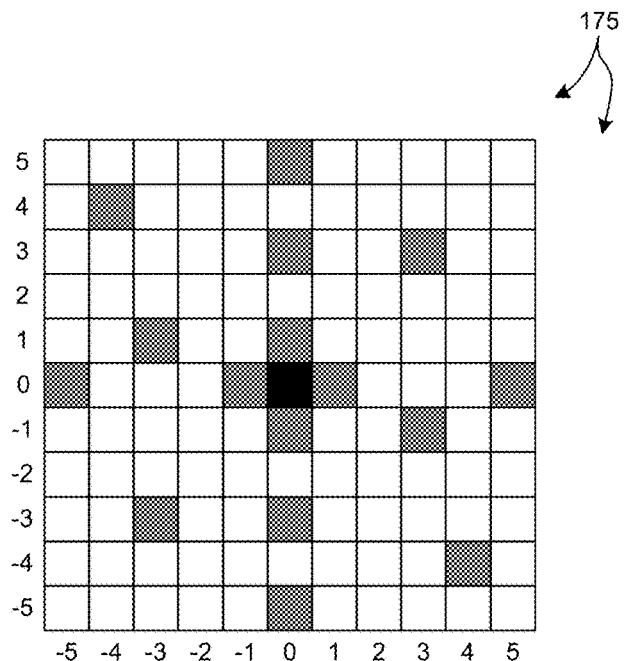
FIG. 5B depicts a relatively sparse truncation order sampling pattern 175.

An example of a relatively dense truncation order sampling pattern 170 is illustrated in FIG. 5A. For each wavelength, multiple truncation orders are computed for each spatial dimension of the structure under measurement. Sampling pattern 170 illustrates a relatively dense sampling pattern from eleven possible truncation orders in two different dimensions (i.e., 11x11 truncation order). In contrast, FIG. 5B depicts a relatively sparse truncation order sampling pattern 175. In general, any number of different truncation orders and sampling patterns may be applied at each different wavelength of the simulated measurement signals.

In some examples, parameter based principle component analysis (PCA) is employed to determine the truncation order pattern for each coarse measurement signal. In these examples, PCA analysis is performed to quantify the relative contribution of each truncation order cell (e.g., cells depicted in FIGS. 5A-5B), on data obtained during a corresponding high truncation order signal simulation. In this manner, truncation order cells with relatively large contributions to accurate signal reconstruction are identified and used during simulations of coarse measurement signals.

In another example, measurement transformation module 150 transforms coarse measurement signals 141 of one type to physically meaningful signals of another type required for successful measurement.

In one example, measurement transformation module 150 generates physically meaningful signals (e.g., 12x12 truncation order) of a SE measurement of a cross grating structure (e.g., SRAM) at zero and ninety degree azimuth angles based on low truncation order signals from two different subsystems. In one example, this is achieved based on a simulation of SE measurements at zero degree azimuth and 12x0 truncation order, and a simulation of SE measurement at ninety degree azimuth angle and 0x12 truncation order. The first set of simulated SE measurements primarily provides information on the bottom grating. The second set of simulated SE measurements primarily provides information on the top grating.

In another example, measurement transformation module 150 transforms multiple coarse measurement signals of one or more different types to physically meaningful signals of another different type required for successful measurement.

Figure 6:
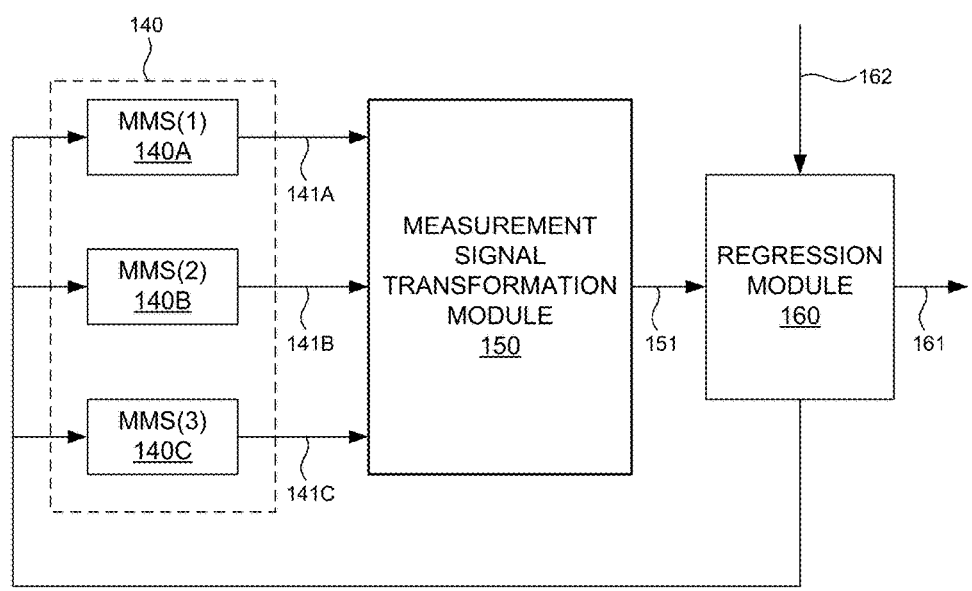
FIG. 6 depicts an example of MMS 140 including three different measurement model simulator sub-modules.

FIG. 6 depicts an example of MMS 140 including three different measurement model simulator sub-modules 140A-C labeled MMS(1), MMS(2), and MMS(3), respectively. Each MMS sub-module is configured to simulate a different type of measurement signal. In this example, MMS(1) is a RCWA engine configured to simulate a SE measurement at zero azimuth angle with a 5x5 truncation order. MMS(2) is a RCWA engine configured to simulate a SE measurement at a forty five degree azimuth angle with 5x5 truncation order. MMS(3) is a RCWA engine configured to simulate a spectroscopic reflectometer (SR) measurement with 3x1 truncation order. MMS(1), MMS(2), and MMS(3) generate coarse measurement signals 141A-C, respectively.

Measurement signal transformation module 150 transforms these signals into a SE measurement signal 151 at a ninety degree azimuth angle with a 12x12 truncation order. Transformed signals 151 are employed as part of a regression analysis to arrive at estimated values 161 of parameters of interest as described with reference to FIG. 2.

In general, any combination of aforementioned examples can be employed to perform model based measurements using measurement signal transformation module 150.

In block 203, regression module 160 receives measured signals 162. In some embodiments, measured signals 162 are detected by a spectroscopic measurement system (e.g., spectrometer 104 depicted in FIG. 1) configured to perform spectroscopic measurements of a specimen (e.g., structure 114). In these embodiments, MMS 140 is configured to simulate the spectroscopic measurements of the specimen performed by the spectroscopic measurement system.

In block 204, regression module 160 perform a regression analysis to estimate one or more parameters of interest of the specimen based on a fitting of the transformed measurement signals 151 to the measured signals 162. This would otherwise not be possible based on coarse measurement signals 141. Regression module 160 iteratively calls upon MMS 140 to simulate the measurement model with different parameter values until convergence of estimated values of the parameters of interest. At each iteration, the coarse measurement signals generated by MMS 140 are transformed by measurement signal transformation module 150 to generate transformed measurement signals 151 that are sufficiently accurate to enable convergence of the regression.

Figure 7:
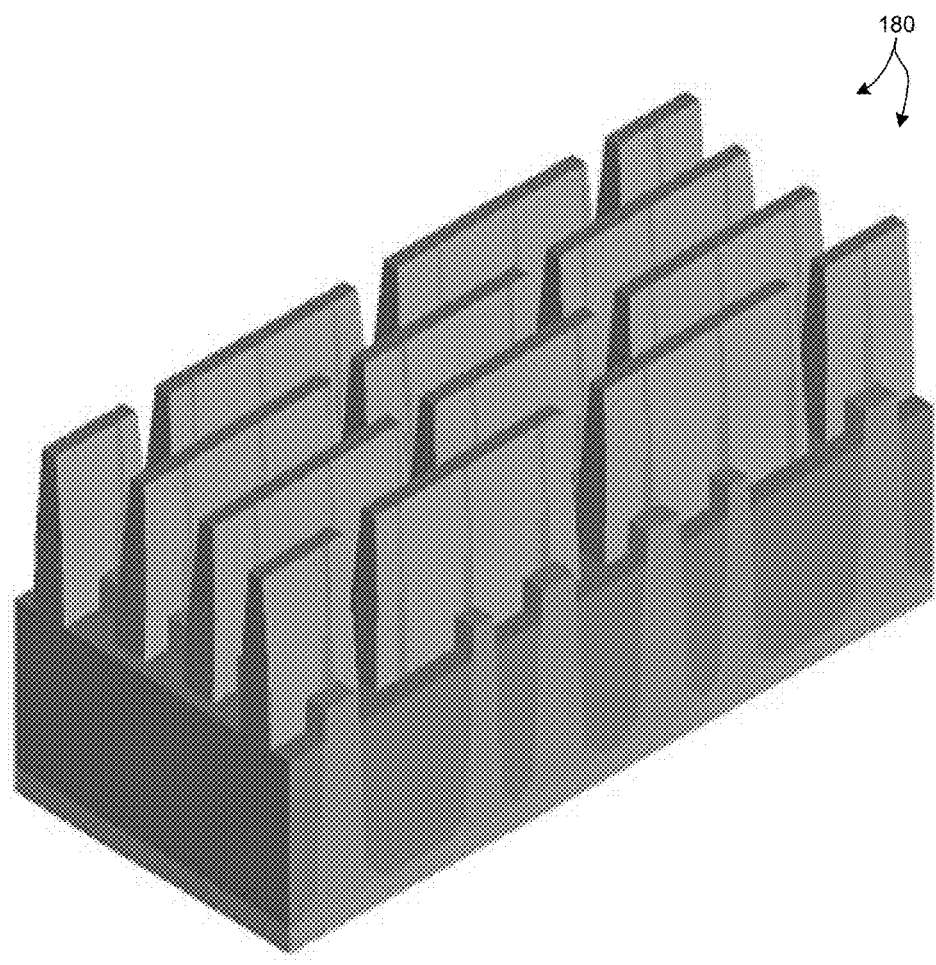
FIG. 7 depicts a structure 180 subject to spectroscopic ellipsometry measurement.
Figure 8:
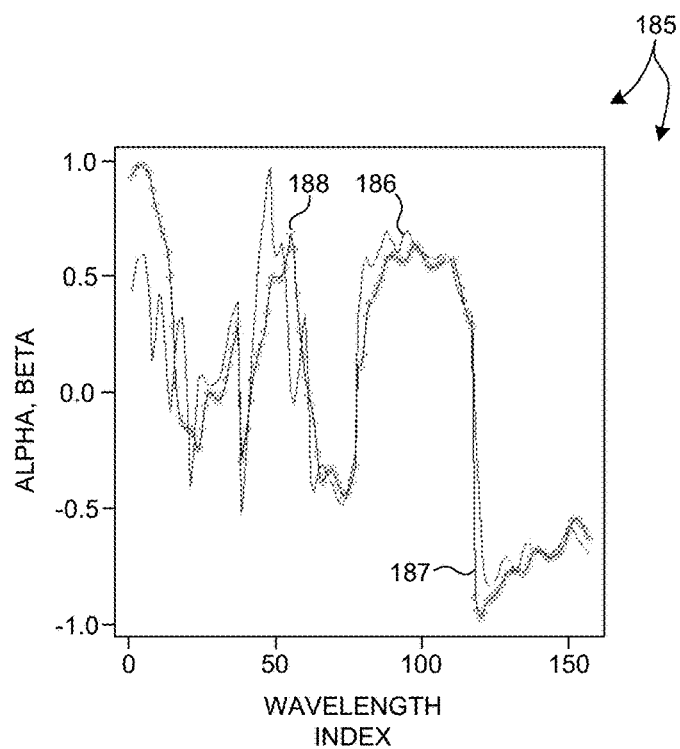
FIG. 8 depicts a plot of coarse measurement signals 186, transformed measurement signals 187, and measured signals 188 for a particular measurement sample of structure 180 within a process window.
Figure 9:
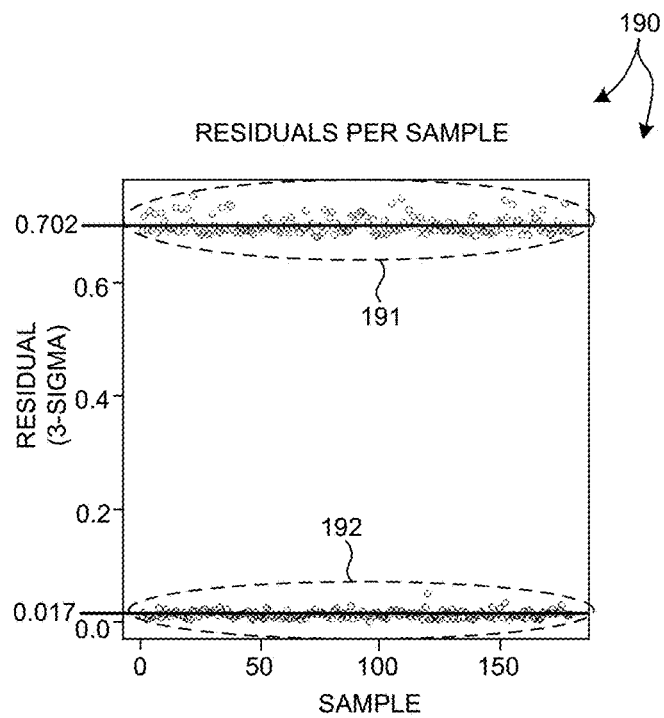
FIG. 9 depicts the 3-sigma values of residual errors for a number of different samples of structure 180 depicted in FIG. 7 within the process window.

FIGS. 8 and 9 depict simulation results indicative of the improvement in the accuracy of signal reconstruction using measurement signal transformation module 150. FIG. 8 depicts a plot of coarse measurement signals 186, transformed measurement signals 187, and measured signals 188 for a particular measurement sample within a process window. These measurement signals are alpha and beta SE measurement signals from SE measurements of structure 180 depicted in FIG. 7. In this example, the coarse measurement signals are generated by a RCWA engine with a 2x4 truncation order. Transformed measurement signals 187 are generated by measurement signal transformation module 150 based on coarse measurement signals 186. Measured signals 188 are simulated SE signals generated by a RCWA engine with a 7x10 truncation order.

As depicted in FIG. 8, the residual differences between coarse measurement signals 186 and measured signals 188 are significant, while the residual differences between transformed measurement signals 187 and measured signals 188 are quite small.

FIG. 9 depicts the 3-sigma values of residual errors for a number of different samples of structure 180 depicted in FIG. 7 within the process window. The cloud of points 191 illustrate the 3-sigma values of the residual errors between coarse measurement signals 186 and measured signals 188 for each sample. As depicted in FIG. 9, the 3-sigma value of this residual error is 0.702. The cloud of points 192 illustrate the 3-sigma values of the residual differences between transformed measurement signals 187 and measured signals 188 for each sample. As depicted in FIG. 9, the 3-sigma value of this residual error is 0.017. In this example, the computational effort associated with the simulation of the measured signals 188 was more than 300 times greater than the computation effort associated with the simulation of the coarse measurement signals 186.

In a further aspect, a measurement signal transformation model is trained to compute transformed measurement signals from coarse measurement signals. Machine learning is used to determine the relationship between coarse measurement signals and corresponding physical signals, and train the measurement signal transformation model based on a DOE training set of data. In this manner, a mathematical function relating coarse measurement signals to transformed signals that accurately reconstruct corresponding physical measurement signals is obtained.

Figure 4:
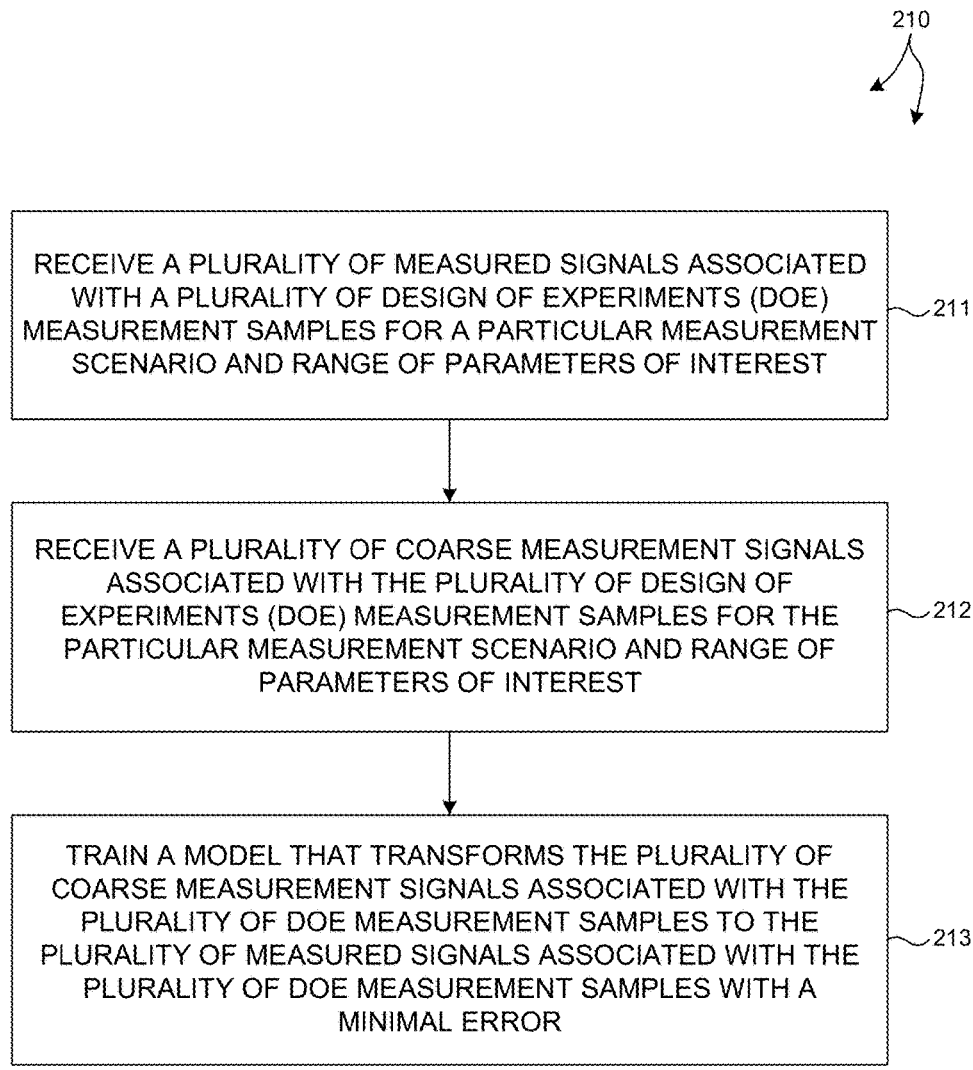
FIG. 4 illustrates a method 210 suitable for implementation by computing system 116 of metrology system 100 illustrated in FIG. 1 of the present invention.

FIG. 4 illustrates a method 210 suitable for implementation by computing system 116 of metrology system 100 illustrated in FIG. 1 of the present invention. In one aspect, it is recognized that data processing blocks of method 210 may be carried out via a pre-programmed algorithm executed by one or more processors of computing system 116, or any other general purpose computing system. It is recognized herein that the particular structural aspects of metrology system 100 do not represent limitations and should be interpreted as illustrative only.

In block 211, computing system 116 receives a plurality of measured signals 113 associated with a plurality of Design Of Experiments (DOE) measurement samples for a particular measurement scenario and range of parameters of interest. The DOE data set is defined for at least one structure or process parameter for a given process window. In some examples the measured signals are actual measurement signals from each DOE point in the DOE sample set. In some other examples, the measured signals are simulated measurement signals that accurately represent the physical signals that would result from an actual measurement for each DOE point in the DOE sample set. In some of these examples, the measured signals are simulated measurement signals based on a RCWA engine at high truncation order.

In block 212, computing system 116 receives a plurality of coarse measurement signals associated with the plurality of Design Of Experiments (DOE) measurement samples for the particular measurement scenario and range of parameters of interest. In some examples, the coarse measurement signals are simulated measurement signals based on a RCWA engine at low truncation order for each DOE point in the DOE sample set.

In block 213, computing system 116 trains the measurement signal transformation model based on the DOE training data. The training is performed such that the measurement signal transformation model transforms the plurality of coarse measurement signals associated with the plurality of DOE measurement samples to the plurality of measured signals associated with the plurality of DOE measurement samples with a minimal error. In some embodiments, the measurement signal transformation model is implemented as a neural network model. In other examples, the measurement signal transformation model may be implemented as a linear model, a polynomial model, a response surface model, a support vector machines model, or other types of models.

In some examples, the sampling size for construction of the measurement signal transformation model is adaptive in the sampling density of the training set size. In one example, the training set size may be initially small and subsequently increase until model transformation convergence. In some examples, convergence may be determined by the transformation model rank. In some examples, convergence may be determined by the post-transform residual errors.

A plurality of conditions for simulating signals exists for each system. In some examples, the minimum set is determined by selecting an optimum set with respect to the measurement signal model from coarse measurement signals to transformed measurement signals, or vice-versa. In one example, an optimum azimuth is selected for measurement and simulations at the azimuth angle where the transformation model has the best ranking relative to other azimuth angles.

In some examples, a secondary set of parameters is used for selecting the optimum system transformation model for each set of selected system parameters used for model generation. In one example of an ellipsometer system, a specific set of wavelengths is selected for each selected azimuth angle during model creation to optimize model fidelity.

In a further aspect, the set of DOE signals employed for model training can be based on actual measurements or simulations of measurements performed by one or more different measurement systems. By way of non-limiting example, any combination of different measurement systems including a spectroscopic ellipsometer (including Mueller matrix and angle resolve implementations), a spectroscopic reflectometer, an X-Ray measurement system, an imaging system, and a two dimensional beam profile reflectometry system may be contemplated within the scope of this patent document. In these examples, approximations specific to each system may be employed.

In another aspect, a combination of different simulators may be employed to compute measurement signals as described herein. In some examples, the type of simulator employed to generate coarse measurement signals is different from the type of simulator employed to generate measured signals that accurately reconstruct physical measurement signals. Although an RCWA solver is described herein, in some cases it is desirable to employ a different solver, particularly to generate measured signals that accurately reconstruct physical measurement signals. In some examples, RCWA may not converge fast enough for some structures of interest even when using high truncation order. By way of non-limiting example, any combination of solvers such as a finite-element-method (FEM), volume integral, surface integral, a finite-difference, time-domain (FDTD) method, or hybrid formulations of these methods and RCWA may be contemplated.

In another aspect, the measurement signals described may include derivatives of measurement signals with respect to parameters of interest or system parameters. In some examples, it may be desirable to compute derivatives of measurement signals with respect to parameters either characterizing the structure (such as CD, film thicknesses, etc.) or system (angles, wavelength, etc.). These derivatives may be used for regression or other fitting algorithms.

In another aspect, both measurement signals and derivatives are computed using high truncation order RCWA or another high accuracy solver for model training, and use low truncation order RCWA or another lower accuracy solver for production library generation and regression.

In another aspect, a measurement signal transformation model is employed to compute transformed measurement signals from actual measured signals. In addition, coarse measurement signals are computed by a measurement model simulator. The transformed measurement signals more closely approximate the coarse measurement signals than the actual measured signals. The transformed measurement signals are subsequently used for regression, library generation, or other analyses where simulated model based measurement signals are typically employed as part of an effort to characterize structural, material, and process parameters in semiconductor manufacturing.

Figure 10:
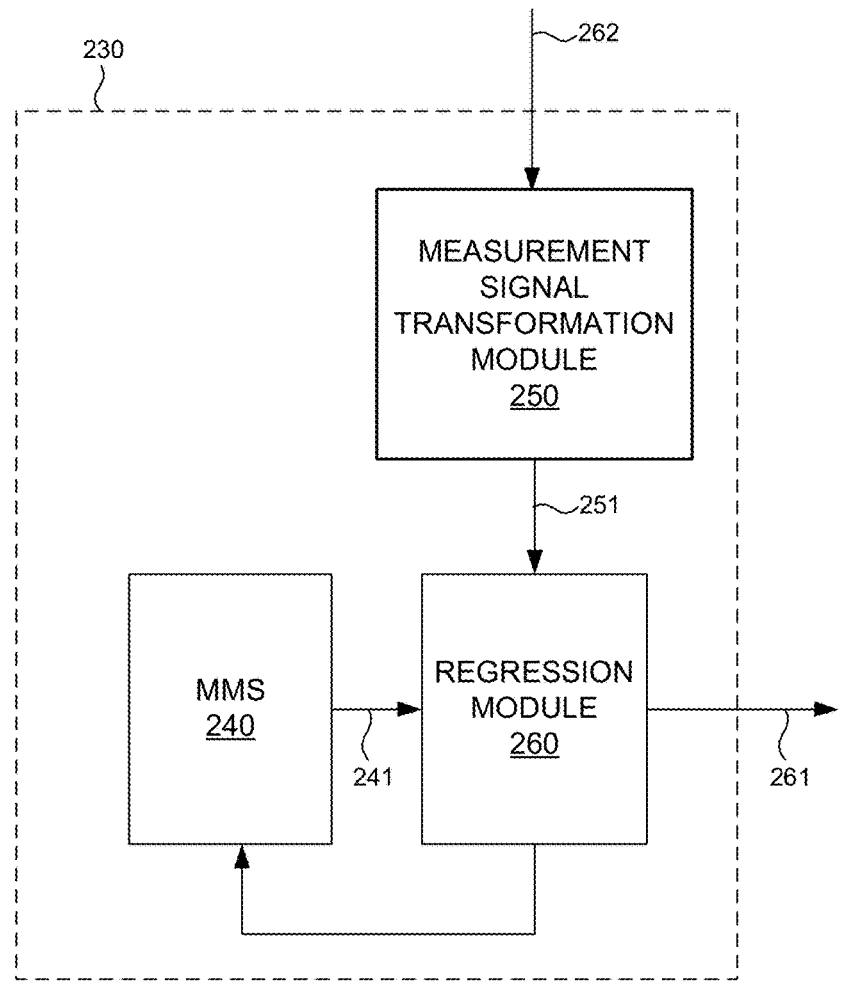
FIG. 10 depicts model based measurement tool 230 in another embodiment.

FIG. 10 depicts model based measurement tool 230 in another embodiment. As depicted in FIG. 10, model based measurement tool 230 includes a measurement model simulator (MMS) 240, measurement signal transformation module 250, and regression module 260. As described with respect to MMS 140 depicted in FIG. 2, MMS 240 is a simulation engine configured to simulate a model of the entire measurement process. In the embodiment depicted in FIG. 10, the measurement signal transformation module 250 transforms actual measured signals 262 to generate transformed measurement signals 261 that more closely approximate the coarse measurement signals 241 than the actual measured signals 262.

The simulation results provided by MMS 240 depend on the configuration of the measurement model itself (e.g., fixed model parameter values, floated model parameters, etc.) and various simulation parameters (e.g., number of slabs, truncation order, truncation pattern, etc.). Model and simulation parameters must be selected such that MMS 240 is able to simulate transformed measurement signals 251 with sufficient accuracy to enable a stable convergence of estimated parameter values 261 by regression module 260.

Figure 11:
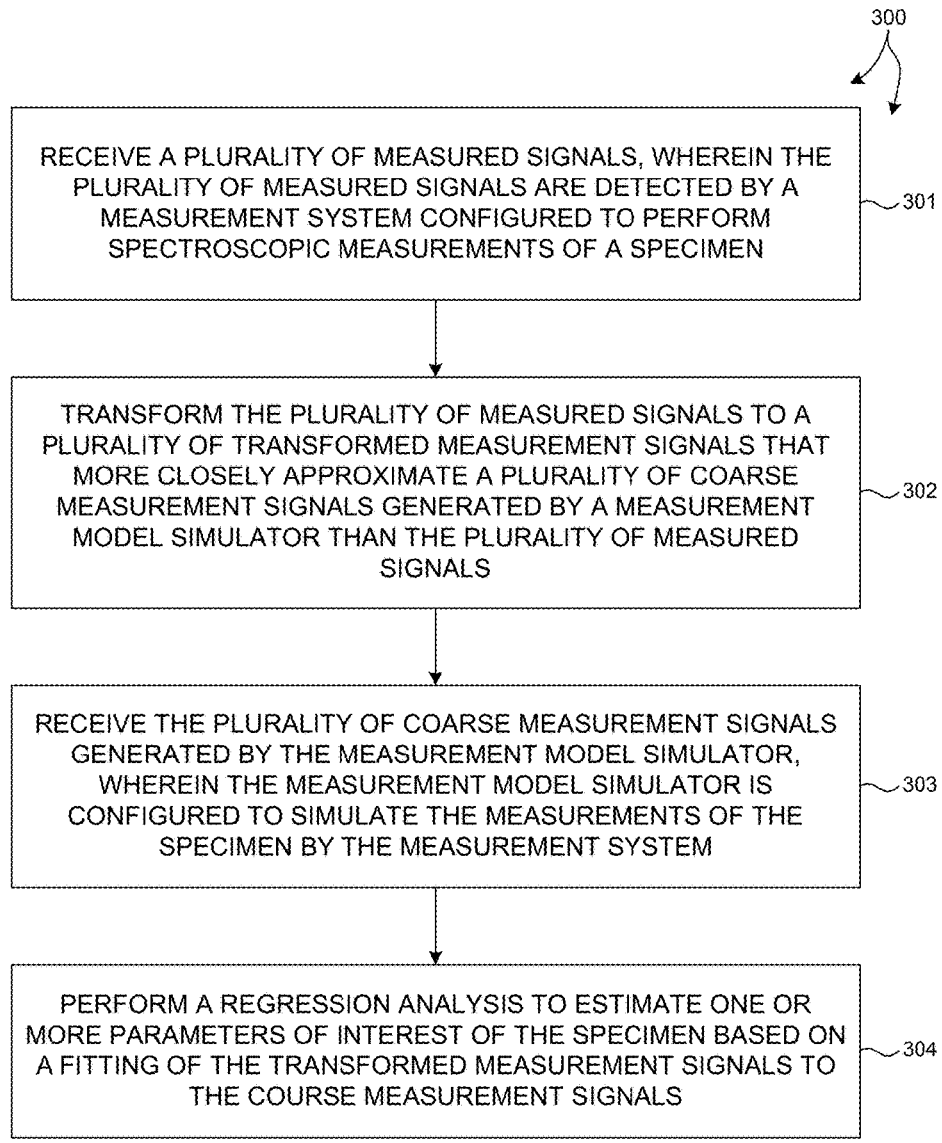
FIG. 11 illustrates a method 300 suitable for implementation by model based measurement tool 230 illustrated in FIG. 10.

FIG. 11 illustrates a method 300 suitable for implementation by model based measurement tool 230 illustrated in FIG. 10 of the present invention. In some embodiments, model based measurement tool 230 is executed by computing system 116 of measurement system 100 depicted in FIG. 1. In one aspect, it is recognized that data processing blocks of method 300 may be carried out via a pre-programmed algorithm executed by one or more processors of computing system 116, or any other general purpose computing system. It is recognized herein that the particular structural aspects of model based measurement tool 230 do not represent limitations and should be interpreted as illustrative only.

In block 301, measurement signal transformation module 250 receives measured signals 262. In some embodiments, measured signals 262 are detected by a spectroscopic measurement system (e.g., spectrometer 104 depicted in FIG. 1) configured to perform spectroscopic measurements of a specimen (e.g., structure 114).

In block 302, measurement signal transformation module 150 transforms the plurality measured signals 262 to a plurality of transformed measurement signals 251 that more closely approximate a plurality of coarse measurement signals generated by MMS 240 than measured signals 262. Transformed measurement signals 251 are sufficiently accurate to ensure stable convergence of estimated parameter values 261 by regression module 260.

In block 303, regression module 260 receives a plurality of coarse measurement signals 241 generated by MMS 240. In these embodiments, MMS 240 is configured to simulate the spectroscopic measurements of the specimen performed by the spectroscopic measurement system. Measurement model and simulation parameters are selected such that MMS 240 generates coarse measurement signals 241 with less computational effort than would be required to generate high accuracy measurement signals. In these examples, the model and simulation parameter settings are suboptimal, yet this selection is made to reduce computational effort.

In block 304, regression module 260 perform a regression analysis to estimate one or more parameters of interest of the specimen based on a fitting of the transformed measurement signals 251 to the coarse measurement signals 241.

Regression module 260 iteratively calls upon MMS 240 to simulate the measurement model with different parameter values until convergence of estimated values of the parameters of interest. At each iteration, the coarse measurement signals generated by MMS 240 are sufficiently accurate to enable convergence of the regression.

In a further aspect, a measurement signal transformation model is trained to compute transformed measurement signals from measured signals. Machine learning is used to determine the relationship between measured signals and coarse measurement signals, and train the measurement signal transformation model based on a DOE training set of data. In this manner, a mathematical function relating measured to transformed signals that accurately reconstruct coarse measurement signals is obtained.

Figure 12:
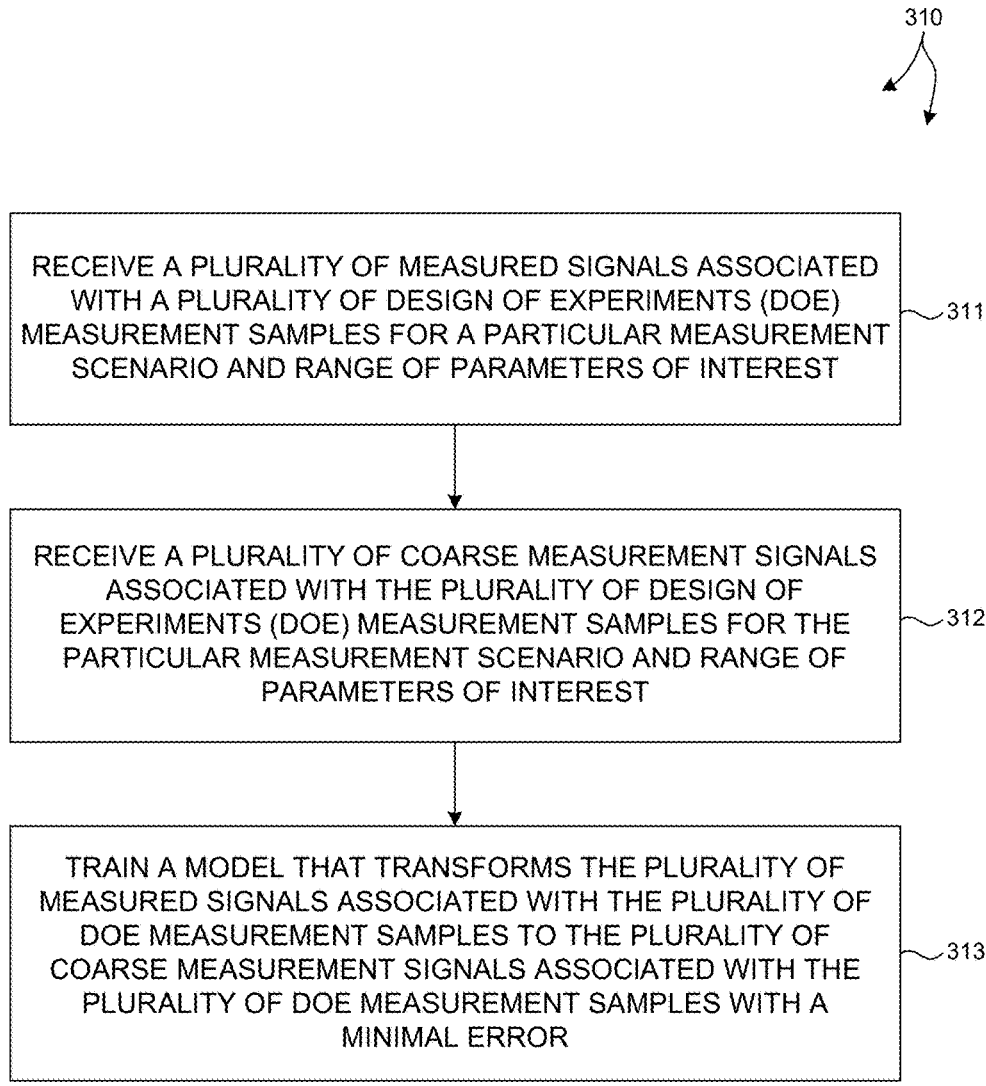
FIG. 12 illustrates a method 310 suitable for implementation by computing system 116 of metrology system 100 illustrated in FIG. 1.

FIG. 12 illustrates a method 310 suitable for implementation by computing system 116 of metrology system 100 illustrated in FIG. 1 of the present invention. In one aspect, it is recognized that data processing blocks of method 310 may be carried out via a pre-programmed algorithm executed by one or more processors of computing system 116, or any other general purpose computing system. It is recognized herein that the particular structural aspects of metrology system 100 do not represent limitations and should be interpreted as illustrative only.

In block 311, computing system 116 receives a plurality of measured signals 113 associated with a plurality of Design Of Experiments (DOE) measurement samples for a particular measurement scenario and range of parameters of interest. The DOE data set is defined for at least one structure or process parameter for a given process window. In some examples the measured signals are actual measurement signals from each DOE point in the DOE sample set. In some other examples, the measured signals used for training are simulated measurement signals that accurately represent the physical signals that would result from an actual measurement for each DOE point in the DOE sample set. In some of these examples, the measured signals are simulated measurement signals based on a RCWA engine at high truncation order.

In block 312, computing system 116 receives a plurality of coarse measurement signals associated with the plurality of Design Of Experiments (DOE) measurement samples for the particular measurement scenario and range of parameters of interest. In some examples, the coarse measurement signals are simulated measurement signals based on a RCWA engine at low truncation order for each DOE point in the DOE sample set.

In block 313, computing system 116 trains the measurement signal transformation model based on the DOE training data. The training is performed such that the measurement signal transformation model transforms the plurality of measured signals associated with the plurality of DOE measurement samples to the plurality of coarse measurement signals associated with the plurality of DOE measurement samples with a minimal error. In some embodiments, the measurement signal transformation model is implemented as a neural network model. In other examples, the measurement signal transformation model may be implemented as a linear model, a polynomial model, a response surface model, a support vector machines model, or other types of models.

In different embodiments of model based measurement tool 230 various approximations of the model, the measurement system, and the simulation engine may be employed. In one example, a measurement signal transformation model 250 is created that transforms measured signals at two azimuth angles (e.g., 0 degrees and 90 degrees) to a low truncation order signal, with a small number of slabs, and no NA sampling.

Although the methods discussed herein are explained with reference to system 100, any optical metrology system configured to illuminate and detect light reflected, transmitted, or diffracted from a specimen may be employed to implement the exemplary methods described herein. Exemplary systems include an angle-resolved reflectometer, a scatterometer, a reflectometer, an ellipsometer, a spectroscopic reflectometer or ellipsometer, a beam profile reflectometer, a multi-wavelength, two-dimensional beam profile reflectometer, a multi-wavelength, two-dimensional beam profile ellipsometer, a rotating compensator spectroscopic ellipsometer, etc. By way of non-limiting example, an ellipsometer may include a single rotating compensator, multiple rotating compensators, a rotating polarizer, a rotating analyzer, a modulating element, multiple modulating elements, or no modulating element.

It is noted that the output from a source and/or target measurement system may be configured in such a way that the measurement system uses more than one technology. In fact, an application may be configured to employ any combination of available metrology sub-systems within a single tool, or across a number of different tools.

A system implementing the methods described herein may also be configured in a number of different ways. For example, a wide range of wavelengths (including visible, ultraviolet, infrared, and X-ray), angles of incidence, states of polarization, and states of coherence may be contemplated. In another example, the system may include any of a number of different light sources (e.g., a directly coupled light source, a laser-sustained plasma light source, etc.). In another example, the system may include elements to condition light directed to or collected from the specimen (e.g., apodizers, filters, etc.).

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), a displacement between two or more structures (e.g., overlay displacement between overlaying grating structures, etc.), and a dispersion property value of a material used in the structure or part of the structure. Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect. However, such terms of art do not limit the scope of the term "metrology system" as described herein. In addition, the metrology system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor processing system (e.g., an inspection system or a lithography system) that may be used for processing a specimen. The term "specimen" is used herein to refer to a site, or sites, on a wafer, a reticle, or any other sample that may be processed (e.g., printed or inspected for defects) by means known in the art. In some examples, the specimen includes a single site having one or more measurement targets whose simultaneous, combined measurement is treated as a single specimen measurement or reference measurement. In some other examples, the specimen is an aggregation of sites where the measurement data associated with the aggregated measurement site is a statistical aggregation of data associated with each of the multiple sites. Moreover, each of these multiple sites may include one or more measurement targets associated with a specimen or reference measurement.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A measurement system comprising:
an illumination source configured to provide an amount of illumination light to one or more metrology targets;
a detector configured to receive an amount of collected light from the one or more metrology targets in response to the amount of illumination light and generate a plurality of measured signals; and
one or more computing systems configured to:
receive the plurality of measured signals from the detector;
receive a plurality of coarse measurement signals generated by a first measurement model simulator, wherein the first measurement model simulator is configured to simulate a measurement of the one or more metrology targets by the measurement system;
transform the plurality of coarse measurement signals to a plurality of transformed measurement signals, wherein a difference between the plurality of transformed measurement signals and the plurality of measured signals is less than a difference between the plurality of coarse measurement signals and the plurality of measured signals; and
perform a regression analysis to estimate one or more parameters of interest of the one or more metrology targets based on a fitting of the transformed measurement signals to the measured signals.

2. The measurement system of claim 1, wherein the transforming of the plurality of coarse measurement signals to the plurality of transformed measurement signals involves a measurement signal transformation model, and wherein the one or more computing systems are further configured to:
receive a plurality of measured signals associated with a plurality of Design Of Experiments (DOE) measurement samples for a particular measurement system configuration and range of parameters of interest;
receive a plurality of coarse measurement signals associated with the plurality of Design Of Experiments (DOE) measurement samples for the particular measurement system configuration and range of parameters of interest; and
train the measurement signal transformation model to transform the plurality of coarse measurement signals associated with the plurality of DOE measurement samples to the plurality of measured signals associated with the plurality of DOE measurement samples with a minimal error.

3. The measurement system of claim 1, wherein the coarse measurement signals are associated a different measurement system configuration than the transformed measurement signals.

4. The measurement system of claim 1, wherein the first measurement model simulator is a rigorous coupled wave analysis (RCWA) simulator.

5. The measurement system of claim 4, wherein the plurality of coarse measurement signals are generated by the RCWA simulator with a reduced truncation order, a reduced number of slabs, a sparse numerical aperture (NA) sample set, or any combination thereof.

6. The measurement system of claim 5, wherein a truncation order number and a truncation order sample set associated with a first portion of the plurality of coarse measurement signals is different from a truncation order number and a truncation order sample set associated with a second portion of the plurality of coarse measurement signals.

7. The measurement system of claim 6, wherein the first portion of the plurality of coarse measurement signals is associated with a first range of wavelengths and the second portion of the plurality of coarse measurement signals is associated with a second range of wavelengths that is different from the first range of wavelengths.

8. The measurement system of claim 1, wherein the coarse measurement signals are associated with multiple, different measurement system configurations.

9. The measurement system of claim 8, wherein the multiple, different measurement system configurations include different measurement angles, different illumination angles, different measurement techniques, or any combination thereof.

10. The measurement system of claim 1, wherein the transformed measurement signals include derivatives of the coarse measurement signals with respect to one or more parameters of interest, one or more measurement system parameters, or any combination thereof.

11. A measurement system comprising:
an illumination source configured to provide an amount of illumination light to one or more semiconductor structures;
a detector configured to receive an amount of collected light from the one or more semiconductor structures in response to the amount of illumination light and generate a plurality of measured signals associated with a measurement of the one or more semiconductor structures by the measurement system; and
a measurement signal transformation module comprising computer-readable instructions stored on a non-transitory, computer-readable medium, the computer-readable instructions comprising:
code for causing a computing system to receive a plurality of coarse measurement signals generated by a first measurement model simulator, wherein the first measurement model simulator is configured to simulate measurements of the one or more semiconductor structures by the measurement system;
code for causing the computing system to transform the plurality of coarse measurement signals to a plurality of transformed measurement signals, wherein a difference between the plurality of transformed measurement signals and the plurality of measured signals is less than a difference between the plurality of coarse measurement signals and the plurality of measured signals; and
code for causing the computing system to estimate one or more parameters of interest associated with the one or more semiconductor structures based on a fitting of the transformed measurement signals to the measured signals.

12. The measurement system of claim 11, the measurement signal transformation module further comprising computer-readable instructions stored on the non-transitory, computer-readable medium, the computer-readable instructions further comprising:
code for causing the computing system to receive the plurality of measured signals associated with the measurements of the one or more semiconductor structures by the one or more measurement systems; and
code for causing the computing system to perform a regression analysis to estimate the one or more parameters of interest of the one or more semiconductor structures.

13. The measurement system of claim 11, wherein the plurality of measured signals are associated with spectroscopic measurements of the one or more semiconductor structures by the measurement system.

14. The measurement system of claim 11, wherein the plurality of measured signals are generated by a second measurement model simulator that is different from the first measurement model simulator.

15. The measurement system of claim 11, wherein the coarse measurement signals are associated a different measurement system configuration than the transformed measurement signals.

16. The measurement system of claim 11, wherein the transforming of the plurality of coarse measurement signals to the plurality of transformed measurement signals involves a measurement signal transformation model, the measurement signal transformation module further comprising computer-readable instructions stored on the non-transitory, computer-readable medium, the computer-readable instructions comprising:
code for causing the computing system to receive a plurality of measured signals associated with a plurality of Design Of Experiments (DOE) measurement samples for a particular measurement system configuration and range of parameters of interest;
code for causing the computing system to receive a plurality of coarse measurement signals associated with the plurality of Design Of Experiments (DOE) measurement samples for the particular measurement system configuration and range of parameters of interest; and code for causing the computing system to train the measurement signal transformation model to transform the plurality of coarse measurement signals associated with the plurality of DOE measurement samples to the plurality of measured signals associated with the plurality of DOE measurement samples with a minimal error.

17. A measurement system comprising:

an illumination source configured to provide an amount of illumination light to one or more semiconductor structures;

a detector configured to receive an amount of collected light from the one or more semiconductor structures in response to the amount of illumination light and generate a plurality of measured signals associated with a measurement of the one or more semiconductor structures by the measurement system; and a measurement signal transformation module comprising computer-readable instructions stored on a non-transitory, computer-readable medium, the computer-readable instructions comprising:

code for causing a computing system to receive the plurality of measured signals;

code for causing the computing system to transform the plurality of measured signals to a plurality of transformed measurement signals, wherein a difference between the plurality of transformed measurement signals and the plurality of measured signals is less than a difference between a plurality of coarse measurement signals and the plurality of measured signals, wherein the plurality of coarse measurement signals are generated by a measurement model simulator; and code for causing the computing system to estimate one or more parameters of interest of the one or more semiconductor structures based on a fitting of the transformed measurement signals to the coarse measurement signals.

18. The measurement system of claim 17, the measurement signal transformation module further comprising computer-readable instructions stored on the non-transitory, computer-readable medium, the computer-readable instructions further comprising:

code for causing the computing system to receive the plurality of coarse measurement signals generated by the measurement model simulator, wherein the measurement model simulator is configured to simulate the measurements of the one or more semiconductor structures by the measurement system, wherein the estimating of the one or more parameters of interest involves a regression analysis.

19. The measurement system of claim 17, wherein the measured signals are associated a different measurement system configuration than the transformed measurement signals.

20. The measurement system of claim 17, wherein the transforming of the plurality of coarse measurement signals to the plurality of transformed measurement signals involves a measurement signal transformation model, the measurement signal transformation module further comprising computer-readable instructions stored on the non-transitory, computer-readable medium, the computer-readable instructions comprising:

code for causing the computing system to receive a plurality of measured signals associated with a plurality of Design Of Experiments (DOE) measurement samples for a particular measurement system configuration and range of parameters of interest;

code for causing the computing system to receive a plurality of coarse measurement signals associated with the plurality of Design Of Experiments (DOE) measurement samples for the particular measurement system configuration and range of parameters of interest; and code for causing the computing system to train the measurement signal transformation model to transform the plurality of measured signals associated with the plurality of DOE measurement samples to the plurality of coarse measurement signals associated with the plurality of DOE measurement samples with a minimal error.

* * * * *